United States Patent [19]

Courier de Méré

[11] 4,161,387

[45] Jul. 17, 1979

[54] DETECTION DEVICES ESPECIALLY FOR THE DETECTION OF FLAMES

[75] Inventor: Henri E. Courier de Méré, Paris, France

[73] Assignee: BICOSA Societe de Recherches, Clichy, France

[21] Appl. No.: 846,080

[22] Filed: Oct. 27, 1977

[30] Foreign Application Priority Data

Apr. 19, 1977 [FR] France .................... 77 11712

[51] Int. Cl.² .................................. F23N 5/00
[52] U.S. Cl. .......................... 431/74; 431/66; 431/75
[58] Field of Search .............. 431/74, 66, 78, 80, 431/75

[56] References Cited

U.S. PATENT DOCUMENTS

| | | | |
|---|---|---|---|
| 3,635,018 | 1/1972 | De Corso et al. ............ | 431/75 X |
| 3,958,791 | 5/1976 | Carlson .................... | 431/74 |
| 3,975,136 | 8/1976 | Baysinger et al. .......... | 431/74 |
| 4,015,928 | 4/1977 | Carlson .................... | 431/74 |
| 4,033,711 | 7/1977 | Christian et al. .......... | 431/66 |

Primary Examiner—Edward G. Favors
Attorney, Agent, or Firm—Morris Liss; Israel Gopstein

[57] ABSTRACT

A detection device comprising two spark-gap electrodes connected to a voltage pulse source having an amplitude greater than the striking voltage of the spark-gap, so that each pulse produces a spark between said electrodes. Such a detection device is characterized in that it comprises, connected to at least one of the electrodes, a detection circuit able to supply at its output a signal whose amplitude is representative of a definite condition of the atmosphere present between said electrodes, particularly of the presence or of the absence, between the electrodes, of an ionized gas such as a flame.

Main uses: devices for the generation of sparks for igniting a fuel.

7 Claims, 5 Drawing Figures

DETECTION DEVICES ESPECIALLY FOR THE DETECTION OF FLAMES

The present invention relates to a detector device of the kind having two spark-gap electrodes connected to a voltage source whose amplitude is greater than the breakdown voltage of the spark-gap so that each pulse produces a spark between said electrodes.

During researches carried out by the applicant on spark-gaps, intented in particular for the generation of sparks for igniting a fuel gas, and on circuits capable of sensing the presence or the absence of a flame, it was discovered that, in the absence of a flame between the electrodes of the spark-gap and more generally in the absence of ionised gas in this gap, the spark-gap behaved not only as receiver of energy but also as a generator of ionisation interference signals (noise), at a high frequency, characterised by an extremely short build-up time, this interference being much less detectable in the presence of ionised gas (e.g. a flame).

The present invention has consequently as an object to use this phenomenon, and the inventive idea which has led thereto is to use such a spark-gap as device for detecting the condition of the atmosphere in the gap between the two electrodes.

In accordance with the invention, consequently, a device of the type mentioned at the beginning will be characterised in that it comprises, connected to at least one of the electrodes, a detecting circuit able to supply at its output a signal whose amplitude is representative of a definite condition of the atmosphere between said electrodes, particularly of the presence or of the absence, between the electrodes, of an ionised gas such as a flame.

Advantageously, said detecting circuit may comprise furthermore at least one inversely connected diode, advantageously followed by an integrator stage.

The diode, e.g. a Zener diode, will in fact conduct the brief transistory signals, with high frequency components, representing the non ionised condition of the gap between the electrodes and will substantially stop, on the other hand, the pulse signals with lower frequency component and with a much smaller amplitude, detectable in the presence of an ionised gas.

Since the amplitude of the interference signals is very definitely greater in the absence of ionised gas between the electrodes of the spark-gap, than in its presence, it is to be noted that this arrangement presents furthermore the advantage of not being subjected to a critical choice of the value of the different components and particularly of the inverse voltage of the diode. The use of a Zener diode will have the extra advantage that the voltage supplied at the detection output is always the same.

As for the integrator stage, permitting the output signal to be conveniently used, it can of course be conventional, e.g. comprise a resistor and a capacitor.

Since the voltages between the electrodes of a spark-gap may be fairly high, it will be advantageous moreover for said detecting circuit to be connected to the terminals of a resistor connected in series with the spark-gap, particularly between one of its electrodes and earth.

Thus, a relatively low resistance resistor may be chosen and, since it will be subjected to relatively low voltages, there will be no particular insulation problem.

As a modification, said detecting circuit could be connected to one of the electrodes of the spark-gap through a coupling capacitor.

A device in accordance with the invention can of course find a great number of applications.

Among others there can be mentioned that which would consist in using such a device in association with a circuit for supplying a burner with fuel gas, as a safety measure, to control for exemple the closure of an electromagnetic valve in said supply circuit in case the flame is accidentally put out.

Such a device could also be used in a fuel gas ignition circuit to control the stopping of the generation of ignition sparks as soon as a flame is present between the electrodes of the spark-gap, a circuit equipped in this way being able then to be advantageously provided in an entirely self-contained gas heating radiator, or else in a lighter, to economise the current source (primary or secondary cell).

The invention has then generally as its object a device comprising particularly a circuit for supplying a burner with fuel gas and/or a circuit for generating fuel ignition sparks, characterised in that it is associated with a detection device such as defined above and in that the ouput signal of said detection circuit is used as a control signal for the operation of said fuel gas supply circuit and/or of said spark generation circuit.

The invention relates more particularly, but not exclusively, among other devices of the above defined type, to those applying furthermore at least some of the arrangements described and/or claimed in French patent application filed on 15 July 1976 under the No. 76 21669 to which correspond:

U.S. patent application Ser. No. 815,408 filed July 13, 1977

Bristish patent application No. 29 463 filed July 13, 1977

Japanese patent application No. 84 300 filed July 15, 1977

A device in accordance with the invention for the generation of sparks for igniting a fuel can thus comprise an oscillator, means for transforming the signals of the oscillator into DC voltage pulses, supplying the electrodes of the spark-gap, particularly through a step-tup transformer, and means for inhibiting the operation of the oscillator, receiving on the one hand a signal representing the presence of a voltage pulse at the output and, on the other hand, a signal able to have two different levels, representing repectively the absence and the presence of a flame between said electrodes, the arrangement of said inhibiting means being achieved so that the operation of the oscillator and consequently the generation of sparks are stopped if the second signal mentioned occupies that of the two said levels which represents the presence of said flame. Such a device will then be characterised in that said signal able to have two different levels is picked up at the output of a detecting device of the type specified at the beginning of the present description, preferably, but not exclusively, of the type comprising an input resistor connected between one of said electrodes and earth.

Different embodiments of the invention are described herebelow as examples in no way limiting, with reference to the figures of the accompanying drawings in which.

Figure 1:
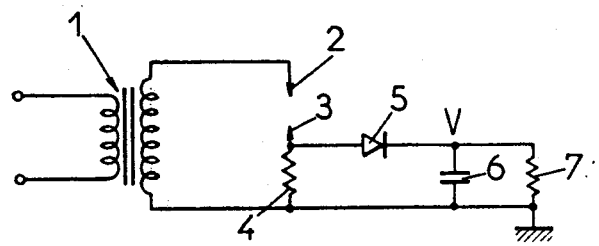
FIGS. 1 and 2 show two different circuits for a spark-gap detecting device in accordance with the invention.
Figure 2:
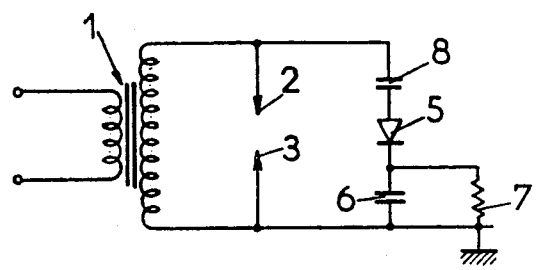

In the detecting device shown in FIGS. 1 and 2, only the output stage is shown, i.e. a step-up transformer 1, electrodes 2 and 3 of the spark-generating spark-gap and the detecting circuit.

The primary of transformer 1 is of course connected to a source—of any kind—of DC pulses, having an amplitude sufficient for the pulses transmitted to the secondary to be of a voltage higher than the breakdown voltage of spark-gap 2-3.

In the case of FIG. 1, the detecting circuit comprises a resistor 4 of some tens of ohms for example connected between electrode 3 and ground. The current pulses passing through this resistor will then give at its terminals voltage pulses, e.g. negative pulses, which will be detected by an inversely connected diode 5, and integrated by a capacitor and resistor unit 6-7.

Figure 3:
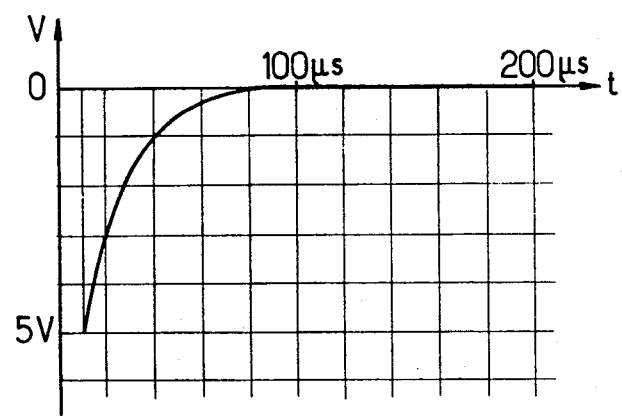
FIGS. 3 and 4 are oscillograms.
Figure 4:
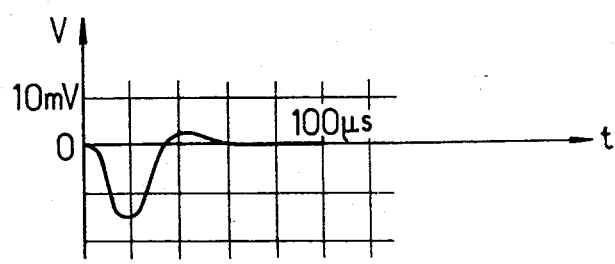

FIG. 3 shows the wave-form of the voltage V detected by the diode 5 when a flame or ionised gas is absent from the gap between electrodes 2 and 3, whereas FIG. 4 shows the wave-form of the same voltages (it is constituted, of course, by a series of pulses) when such a gas or flame is present therein.

It can be seen that the wave-form and the amplitude of the pulses, are very different in the two cases (5 volts and more in the case of FIG. 3 and 15 mV in the case of FIG. 4, of course all things being otherwise equal).

This is due to the fact that in the first case, spark-gap 2,3 behaves like an HF noise source, i.e. generales high amplitude pulses and with very brief build-up time readily transmitted by diode 5 (whose inverse conduction voltage is of course chosen in consequence), whereas in the second case-the presence, between the electrodes, of an ionised gas or a flame—the pulses are of a much lower amplitude and with components of much lower frequencies, and are therefore almost completely stopped by the diode.

At the output of the integrator circuit, consequently, there will be obtained, as the case may be, signals of very clearly defined levels and this without special precautions as to the choice of the components characteristics.

Consequently, the output signal may be conveniently used for any one of the above mentioned objects, for example to stop the operation of the pulse generator which feeds the primary of the transformer as soon as said signal reaches the value which represents the presence of a flame (low level of the signal).

In the case of FIG. 2, where the same references designate the same element or elements having the same function, as in FIG. 1, there has been shown a modification in which the signal to be detected is picked up from electrode 2 through coupling capacitor 8, with substantially the same pulse voltage wave-forms and the same advantages as in the case of FIG. 1.

Figure 5:
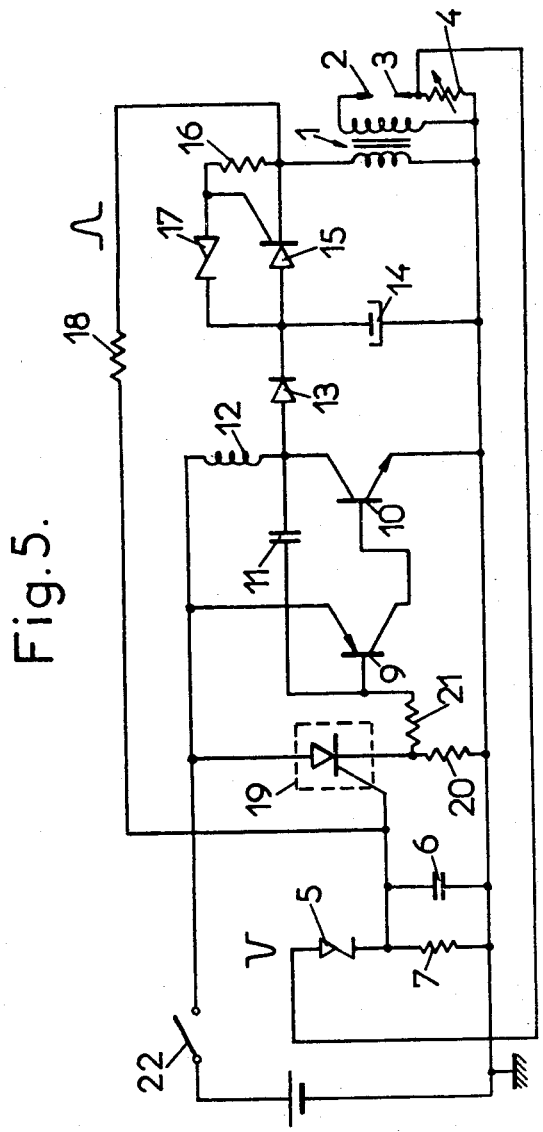
FIG. 5 shows the complete circuit of a device for generating fuel gas ignition sparks, equipped with a detecting device in accordance with the invention.

In FIG. 5, there has been shown the complete electrical circuit of a device for generating sparks for igniting a fuel gas, applicable for example to a lighter equipped with a detecting device in accordance with the invention, comprising electrodes 2 and 3 for the generation of these sparks step-up transformer 1 and components 4,5, 6 and 7 corresponding to the components having the same references in FIG. 1. However, diode 5 has been replaced by a Zener diode.

This device comprises moreover, as already described in the above mentioned French patent application No. 76 21669, an oscillator formed by transistors 9 and 10, capacitor 11 and inductor or coil 12. The A.C. signals produced by this oscillator are rectified and transformed into D.C. pulses fed to the primary of transformer 1, through the circuit comprising diode 13, capacitor 14, discharge thyristor 15, resistor 16 and trip Zener diode 17. Thus there are produced at the primary of transformer 1, positive voltage pulses and, at its secondary, the windings being reversed, negative pulses.

The signals produced at the output of the integrator-detector device 2,3,4,5,6,7 are added to those which appear at the primary of the transformer through loop resistor 18 and are fed to the gate of an inhibiting thyristor 19 whose output, taken from cathode resistor 20, is connected to the base of transistor 9 by a resistor 21.

Thus, at the moment when a positive pulse appears at the primary of transformer 1, if the fuel is not ignited, the negative pulse produced by the detecting device, which appears at capacitor 6, offsets the positive pulse transmitted by resistor 18, and thyristor 19 remains therefore blocked and cannot interrupt the operation of the oscillator and consequently the generation of sparks.

On the other hand, if a flame is present between electrodes 2 and 3, the positive voltage of the primary is not offset by a negative pulse and therefore triggers thyristor 19 causing the oscillator, and consequently the generation of sparks, to be stopped.

Of course, instead of the circuit of FIG. 1, the circuit of FIG. 2 could be used for detecting ionisation interference negative pulses appearing at the spark-gap in the absence of a flame, or any other equivalent circuit.

In any case, the above described circuit presents the advantage, over that which would consist in bringing the signal from electrode 3 (or 2) to diode 5 through a resistor voltage divider, of avoiding any problem of insulation, moreover permitting resistor 4 to be of a low value, being subjected to low voltages of the order of about ten volts.

In addition, the operation of the device is extremely reliable and the choice of components is not critical, as already explained above (resistor 4 may be ajustable).

Another important advantage resides in the fact that a detecting device such as described above does not need the use of a special pick-up, more or less fragile, such as a thermo-couple, a photoelectric cell or similar device for the detection of the flame.

In the example described above the device in accordance with the invention is used to detect the presence or the absence of a flame. However, this device may also be used to detect the presence or absence of an electric arc between electrodes 2 and 3. In fact if the electric arc does not appear (whether a flame is present or not), the voltage between the electrodes reaches a value substantially greater than in the case of spark generation. This arrangement may be used for example to control or not the feed or delivery of gaseous fuel adjacent the electrodes in a boiler. Thus, the comparison with a first threshold allows the fuel feed to be controlled—when it is certain that sparks are produced between the electrodes—and the comparison with a second threshold allows the operation of the ignition device to be stopped (after appearance of the flame).

The device which has just been described in relation to the Figs. can lend itself to numerous applications. Besides the construction of a smoker's lighter (pocket or table lighter), this device may be used for example for monitoring a flame, not only in household but also in industrial installations. The device may also be used in association with an internal combustion engine ignition circuit. In this case, the sparking plug constitutes the spark-gap. With such an ignition circuit, an ignition can be substantially ensured at each cycle. Or course it is necessary to choose the time separating the control of the operation of spark generation at a value compatible with the rotational speed of the engine.

In the FIG. 5 diagram, the triggering of the ignition spark generation is caused by actuating a hand switch 22. It is to be noted that if this diagram, or an equivalent circuit diagram, were applied to the generation of ignition sparks for a fuel in a heating radiator or a boiler, for example, this function of triggering of the sparks could be advantageously assumed by a thermostat supplying the corresponding control for example when the temperature of the environment to be heated drops below a predetermined threshold, at the same time as the control of the fuel delivery.

The stopping of the spark generation would then be carried out automatically through the above-described detecting device, whereas the stopping of the fuel delivery would take place when the temperature reached a higher predetermined threshold. The operation of the assembly would then be entirely automatic.

The invention is of course in no wise limited to the embodiments which have been more particularly considered; it covers, on the contrary, all modifications thereof which are comprised in the scope of the following claims.

I claim:

1. A flame detecting apparatus comprising spark electrodes defining a spark-gap therebetween and connected to a source of voltage pulses of a predetermined polarity, said pulses having an amplitude greater than the breakdown voltage of the spark-gap so that each pulse produces a spark between said spark electrodes, further comprising a detection device responsive to high frequency noise signals generated at each spark, said detecting device comprising a diode having two electrodes, wherein one of said electrodes is coupled to one of said spark electrodes to be connected in inverse conduction relationship with respect to said predetermined polarity of said pulses.

2. A detecting apparatus according to claim 1, wherein a resistor is serially connected between said one spark electrode and said source of voltage pulses and wherein an electrode of said diode is directly connected to said one spark electrode.

3. A detecting apparatus according to claim 1, wherein a coupling capacitor is connected between said one spark electrode and said diode.

4. A detecting apparatus according to claim 1, comprising an integrator stage connected to the other of said diode electrodes which is not coupled to said one spark electrode.

5. A device comprising a circuit for supplying a burner with fuel gas and a circuit for generating ignition sparks for the fuel, characterised in that it is associated with a detection device in accordance with claim 1 and in that the output signal of said detection circuit is used as a signal for controlling the operation of said fuel gas supply circuit and of said spark generation circuit.

6. A device according to claim 5, comprising an oscillator, having an output signal means for transforming the oscillator output signal into D.C. pulses feeding the electrodes of the spark-gap, and means for inhibiting operation of the oscillator, adapted to receive on the one hand a signal representing the presence of a D.C. voltage pulse at the output and, on the other hand, a signal able to have two different levels, representing respectively the absence or the presence of a flame between said electrodes, the arrangement of said inhibiting means being achieved so that the operation of the oscillator and consequently the generation of sparks are stopped if said second signal occupies that of the two said levels which represents the presence of said flame, characterised in that said signal able to have two different levels is picked up at the output of a device in accordance with claim 1.

7. A device according to claim 1, for a gas radiator or a boiler, characterised in that it is associated with a thermostat subjected to the temperature of the environment to be heated and adapted, on the one hand, to cause the triggering of the spark generation and the intake of the fuel if this temperature drops below a first predetermined threshold and, on the other hand, the stopping of the feed of fuel if this temperature reaches a second predetermined threshold, higher than said first level.

* * * * *